(12) United States Patent
Lambroza

(10) Patent No.: US 6,796,993 B2
(45) Date of Patent: Sep. 28, 2004

(54) INFLATABLE TOURNIQUET

(76) Inventor: Arnon Lambroza, 108 E. 82nd St., Apt. 4B, New York, NY (US) 10028

( * ) Notice: Subject to any disclaimer, the term of this patent is extended or adjusted under 35 U.S.C. 154(b) by 55 days.

(21) Appl. No.: 10/066,081

(22) Filed: Jan. 31, 2002

(65) Prior Publication Data
US 2003/0144691 A1 Jul. 31, 2003

(51) Int. Cl.$^7$ ................................................ A61B 17/00
(52) U.S. Cl. ...................................................... 606/202
(58) Field of Search ............................... 606/202, 203, 606/204, 201; 128/96.1

(56) References Cited

U.S. PATENT DOCUMENTS

| | | | |
|---|---|---|---|
| 4,106,002 A | | 8/1978 | Hogue, Jr. ................... 340/626 |
| 4,210,147 A | * | 7/1980 | Nestor et al. ................ 606/202 |
| 4,321,929 A | | 3/1982 | Lemelson et al. ........... 128/630 |
| 4,520,819 A | | 6/1985 | Birmingham et al. ....... 128/327 |
| 4,548,198 A | | 10/1985 | Manes ......................... 128/327 |
| 4,920,971 A | * | 5/1990 | Blessinger ................... 600/492 |
| 5,413,582 A | * | 5/1995 | Eaton .......................... 606/202 |
| 5,464,420 A | * | 11/1995 | Hori et al. ................... 606/202 |
| 6,299,629 B1 | | 10/2001 | Gruenfeld et al. .......... 606/202 |

OTHER PUBLICATIONS

A page headed "84—Fluids and Shock", copied from a textbook entitled, "Emergency Care in the Streets", Second Edition, by Nanacy L. Caroline, M.D., published in Sep. 1982 by Little, Brown and Company, Inc.
Synopsis of Venipuncture Course offered by e–CEUs.com.. A printout of this synopsis sheet was obtained from the internet at http://www.e–CUEs.com. This web page is dated Sep. 2000.

* cited by examiner

Primary Examiner—Kevin T. Truong
(74) Attorney, Agent, or Firm—Morgan, Lewis & Bockius, LLP

(57) ABSTRACT

The present invention provides an inflatable tourniquet including an inflatable occluding band, for placement about a limb of a patient, a pump for inflating the occluding band, wherein the pump is capable of producing sufficient pressure within the occluding band in order to block blood flow in a vein of the patient, a fluid conduit, in fluid communication between the occluding band and the pump, and a pressure relief valve, for releasing the fluid from the occluding band.

3 Claims, 1 Drawing Sheet

INFLATABLE TOURNIQUET

BACKGROUND

1. Field of Invention

The instant invention generally relates to an inflatable tourniquet and the method of use thereof. More particularly, the present invention relates to an inflatable tourniquet to facilitate medical practitioners' drawing of blood and/or starting an intravenous line.

2. State of the Art

The process of drawing blood or starting of an intravenous line requires that a vein of the patient be punctured with an aperture/needle tip. This process, known as venipuncture and performed by medical professionals numerous times a day, is sometimes easy and sometimes not—especially for inexperienced or tentative practitioners, and when performed on elderly or young people, or intravenous drug users.

Each heartbeat consists of a period of cardiac contraction and a period of cardiac relaxation resulting in a pulsating flow of blood, which can be palpated at various arteries in the body, such as the brachial artery in the arm and the radial artery in the wrist. As blood travels through the body, resistance within the blood vessels leads to a continuous decrease in blood pressure throughout the circulatory system. As a result, the large veins of the arm, for instance, have a much lower internal pressure than the arteries that feed these veins. In addition, the walls of the veins are thinner than those of the arteries because they contain less muscle. This combination of lower internal pressures and thinner walls makes veins more easily collapsible.

Under normal conditions, veins are in a near collapsed state and must be distended prior to venipuncture. It has generally been found effective for the medical practitioner to first apply a tourniquet to block the blood flow from the vein, while at the same time allow passage of blood thereto. Presently, medical practitioners utilize an elastic band, tying it to the upper arm to cut off the flow of blood from the vein located at the intersection of the bicep and forearm. However, this procedure sometimes fails, as the pressure applied by the tourniquet may be excessive thereby blocking the flow in the artery that feeds the vein. Conversely, if too little occluding pressure is applied, the vein may partially empty, which leads to inadequate distention. Accordingly, there is a recognized need for a more effective method and apparatus to cut off the flow of blood from the vein, but allow free flow through the artery that feeds the vein.

OBJECTS AND SUMMARY OF THE INVENTION

Accordingly, it is an object of the present invention to provide a method and apparatus for cutting off the flow of blood from a vein while allowing free flow through the artery that feeds the vein.

Another object of the present invention is to provide a tourniquet that may be easily adjusted.

It is a further object of the present invention to provide an inflatable tourniquet and the method of use thereof.

It is a further object of the present invention to provide an inflatable tourniquet for use by medical practitioners in preparation for venipuncture.

It is a further object of the present invention to provide an inflatable tourniquet for use by medical practitioners in the drawing of blood and/or starting an intravenous line.

These and other objects of the present invention will be apparent in the following description.

The present invention provides an inflatable tourniquet including an inflatable occluding band, for placement about a limb of a patient; a pump for inflating the occluding band, wherein the pump is capable of producing sufficient pressure within the occluding band in order to block blood flow in a vein of the patient; a fluid conduit, in fluid communication between the occluding band and the pump; and a pressure relief valve, for releasing the fluid from the occluding band.

The present invention further provides an inflatable tourniquet that does not include a mechanism for measuring blood pressure, yet may include a simple pressure gauge for measuring pressure within the tourniquet.

The present invention further provides a method of preparing a patient for the insertion of a needle into a vein, by providing an inflatable tourniquet including an inflatable occluding band, a pump, and a pressure relief valve; placing the occluding band about a limb of a patient; and inflating the occluding band using the pump, so as to produce sufficient pressure within the occluding band to block blood flow in the vein of the patient.

DETAILED DESCRIPTION

In brief overview, the present invention involves a method and apparatus of providing an inflatable tourniquet to enhance the process of drawing blood, and/or starting an intravenous line, which require that a vein of the patient be punctured with an aperture/needle tip including, but not limited to, a syringe. While finding a vein is generally an easy task with healthy individuals, there is a recognized need for special attention with patients that are elderly, very young, or intravenous drug users. These individuals have thin veins that do not protrude, or have simply collapsed from excessive use. The presently available elastic bands utilized for tying the upper arm to cut off the flow of blood from the vein, sometimes fail because the pressure applied by the tourniquet, if excessive, blocks the flow of blood into the artery that feeds the vein. Conversely, if too little occluding pressure is applied, the vein may partially empty presenting inadequate distention. The present invention overcomes the deficiencies of the prior art by providing an effective method and apparatus to cut off the flow of blood from the vein, while allowing the free flow of blood through the artery that feeds the vein.

Figure 1:
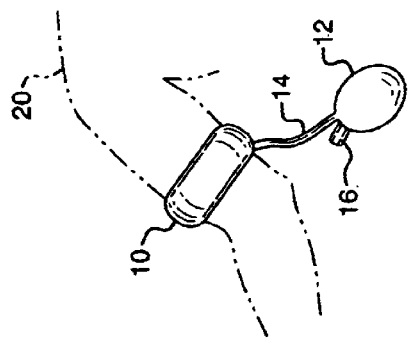
FIG. 1 depicts a preferred embodiment of the present invention as applied to a limb of a patient.
Figure 2:
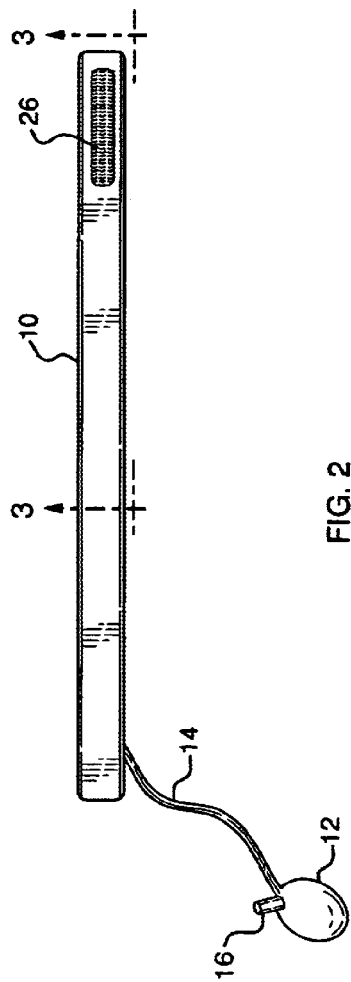
FIG. 2 depicts a top view of the preferred embodiment of the present invention.
Figure 3:
FIG. 3 depicts a partial side view of the preferred embodiment of the present invention take along line 3—3 in FIG. 2.
Figure 4:
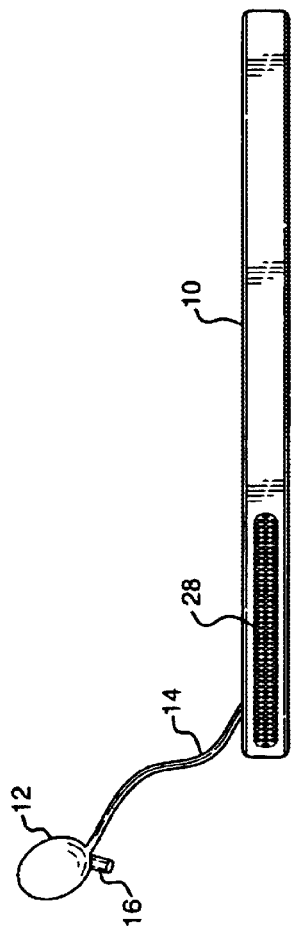
FIG. 4 depicts a bottom view of the preferred embodiment of the present invention.

With reference now to the figures and, in particular, with reference to FIG. 1, there is depicted a representation of the preferred embodiment. The inflatable tourniquet of the present invention generally includes an inflatable occluding band 10, a pump 12, a pressure relief valve 16, and a substantially flexible tube 14 in fluid contact between the occluding band, pump, and valve. The occluding band is generally an elongated rectangular device (FIGS. 2 and 4) that is wrapped about a limb of the patient, as shown for example only in FIG. 1, and may be specifically sized for children or adults. The occluding band includes a closure to hold it firmly on the patient's limb. The closure is preferably an arrangement of hooks 26 and loops 28 (FIGS. 2–4), which allows for variations in the size of the patient's limb. Nevertheless, various other systems may be utilized, such as ties, snaps, belts, elastics, or any other device that would provide the desired closure. The occluding band may also be provided in other shapes, such as a continuous ring or any other shape that would provide the desired result.

Once the occluding band is positioned on the patient's limb, fluid is pumped into it so as to apply a continuous ring of pressure about the limb, which is effective in cutting off the flow of blood out of the veins below the occluding band—but not sufficient to occlude an artery. This is preferably done by initially elevating the pressure above the level required to occlude the artery and slowly relieving the pressure until the vein is distended. The fluid is preferably air, but other fluids may be substituted. The air is pumped into the occluding band using a simple handheld bladder pump, but other pumping devices that provide the desired function may be substituted. The pressure relief valve may be positioned anywhere, as long as it is in fluid communication with the occluding band, such as on the pump, the fluid tube, the occluding band itself, or even on a separate fluid tube.

Once the flow of blood out of the veins is blocked, the pressure builds up engorging the veins close to the obstruction. In this way, the veins become distended and more visible, thereby giving the medical practitioner an easy target. If too much fluid is pumped into the occluding band, the artery that feeds the vein may be blocked. However, unlike conventional tourniquets, the pressure can be released in small increments without removing the tourniquet and starting over. Simply by releasing the fluid via the pressure release valve the flow to the arteries can resume, while the veins remain blocked.

Figure 5:
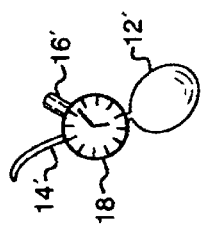
FIG. 5 depicts a partial view of an alternate embodiment of the present invention.

Various techniques may be utilized to attain the optimal occluding band pressure. One technique involves the palpation of the patient's radial artery. The occluding band is inflated until the radial pulse is no longer palpable. The pressure is then slowly released until the pulse just becomes detectable again, at which point no further air is released until the vein distends sufficiently for the medical practitioner to perform the venipuncture. Alternatively, as shown in FIG. 5, the present invention may include an indicator, which can more accurately indicate the presence of a pulse. Additionally, a gauge with a needle, which pulses with each cardiac contraction, may be utilized. The operation of the present invention including a gauge follows the same steps as the above-described technique involving the palpation of the patient's artery. In fact, any indicator including, but not limited to, visual and audio signaling devices may be substituted.

While the foregoing has described and exemplified aspects of various embodiments of the present invention, those skilled in the art will recognize that alternative elements and techniques, and/or combinations and sub-combinations of the described elements and techniques, can be substituted for, or added to, the embodiments and methods described herein. The present invention, therefore, should not be limited to, or defined by, the specific apparatus, methods, and articles-of-manufacture described herein, but rather by the appended claims, which are intended to be construed in accordance with well-settled principles of claim construction, including, but not limited to, the following:

Limitations should not be read from the specification or drawings into the claims (e.g., if the claim calls for a "chair," and the specification and drawings show a rocking chair, the claim term "chair" should not be limited to a rocking chair, but rather should be construed to cover any type of "chair").

The words "comprising," "including," and "having" are always open-ended, irrespective of whether they appear as the primary transitional phrase of a claim, or as a transitional phrase within an element or sub-element of the claim (e.g., the claim "a widget comprising: A; B; and C" would be infringed by a device containing 2A's, B, and 3C's; also, the claim "a gizmo comprising: A; B, including X, Y, and Z; and C, having P and Q" would be infringed by a device containing 3 A's, 2 X's, 3 Y's, Z, 6 P's, and Q).

The indefinite articles "a" or "an" mean "one or more"; where, instead, a purely singular meaning is intended, a phrase such as "one," "only one," or "a single," will appear.

Where the phrase "means for" precedes a function, it is intended that the resulting means-plus-function element be construed to cover any, and all, implementations of the recited function using any standard techniques known by, or available to, persons skilled in the relevant art. A claim that contains more than one means-plus-function element should not be construed to require that each means-plus-function element must be a structurally distinct entity; rather, such claim should be construed merely to require that the overall combination which implements the invention must, as a whole, implement at least the functions called for by the claims.

What is claimed is:

1. A method of facilitating insertion of a needle into a desired vein in a limb of a human subject for intravenous fluid administration or extraction employing an inflatable pressure cuff, a pump connected to said cuff for inflating said cuff, an indicator for indicating a value corresponding to a pressure within said cuff, a valve for selectively reducing the pressure in said cuff, said method comprising:

(a) securing said pressure cuff around the limb containing the desired vein in which the needle is to be inserted;
   (b) inflating said pressure cuff above a systolic pressure of the subject;
   (c) reducing said pressure within said cuff via said valve;
   (d) suspending further reducing of the pressure within said cuff via said valve when said indicator indicates pulses corresponding to cardiac contraction of the subject, whereby the desired vein is in a condition to facilitate needle insertion; and
   (e) inserting the needle into the desired vein.

2. A method as in claim 1, wherein said indicator is a gauge that provides a visual indication of the pressure within said cuff, and wherein step (d) comprises observing when the visual indication varies between higher and lower values.

3. The method in claim 2, wherein said method comprises further relieving the pressure in said cuff after step (e).

* * * * *